US012733929B2

(12) United States Patent
Hibner et al.

(10) Patent No.: US 12,733,929 B2
(45) **Date of Patent: *Sep. 15, 2026**

(54) CIRCULARITY SYSTEMS AND METHODS FOR SURGICAL STAPLERS

(71) Applicant: Cilag GmbH International, Zug (CH)

(72) Inventors: John A. Hibner, Mason, OH (US); Paul Moubarak, Cincinnati, OH (US); Thomas B. Remm, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 19/020,822

(22) Filed: Jan. 14, 2025

(65) Prior Publication Data

US 2025/0152169 A1 May 15, 2025

Related U.S. Application Data

(63) Continuation of application No. 18/345,613, filed on Jun. 30, 2023, now Pat. No. 12,239,318.

(51) Int. Cl.
*A61B 17/068* (2006.01)
*A61B 17/072* (2006.01)
(Continued)

(52) U.S. Cl.
CPC .......... *A61B 17/072* (2013.01); *A61B 17/068* (2013.01); *A61B 17/07207* (2013.01);
(Continued)

(58) Field of Classification Search
CPC ................ A61B 17/072; A61B 17/068; A61B 17/07207; A61B 17/320092; A61B 34/30;
(Continued)

(56) References Cited

U.S. PATENT DOCUMENTS 5,129,570 A * 7/1992 Schulze ........... A61B 17/07207
227/176.1
5,312,023 A 5/1994 Green et al.
(Continued)

FOREIGN PATENT DOCUMENTS

EP 2036505 A1 * 3/2009 ........... A61B 17/068
EP 2036505 B1 * 11/2010 ........... A61B 17/072

*Primary Examiner* — Robert F Long
(74) *Attorney, Agent, or Firm* — Vorys, Sater, Seymour and Pease LLP

(57) ABSTRACT

A method of replacing a consumable of a surgical tool includes securing the surgical tool, which includes a drive housing, a shaft extending from the drive housing, an end effector arranged at a distal end of the shaft and including opposing upper and lower jaws, a wrist interposing the shaft and the end effector, and a knife assembly including a knife arranged at the end effector and first and second drive members extending to the drive housing. The method includes uncoupling the end effector from the wrist, moving the end effector distally from the wrist while the wrist remains intact, removing the knife assembly from the end effector, and thereby entirely separating the end effector from proximal portions of the surgical tool, replacing the consumable of the surgical tool, reconnecting the knife assembly to the surgical tool, and re-coupling the end effector to the wrist.

21 Claims, 10 Drawing Sheets

(51) Int. Cl.

| | |
|---|---|
| ***A61B 17/32*** | (2006.01) |
| ***A61B 34/30*** | (2016.01) |
| *A61B 17/00* | (2006.01) |
| *A61B 17/28* | (2006.01) |
| *A61B 17/29* | (2006.01) |
| *A61B 34/00* | (2016.01) |

(52) U.S. Cl.
CPC ...... *A61B 17/320092* (2013.01); *A61B 34/30* (2016.02); *A61B 17/00234* (2013.01); *A61B 2017/00292* (2013.01); *A61B 2017/00477* (2013.01); *A61B 2017/07214* (2013.01); *A61B 2017/07285* (2013.01); *A61B 17/282* (2013.01); *A61B 2017/2927* (2013.01); *A61B 2017/2929* (2013.01); *A61B 34/71* (2016.02)

(58) Field of Classification Search
CPC . A61B 17/00234; A61B 17/282; A61B 34/71; A61B 2017/00292; A61B 2017/00477; A61B 2017/07214; A61B 2017/07285; A61B 2017/2927; A61B 2017/2929; A61B 18/1445; A61B 2017/00314; A61B 2017/00473; A61B 2018/00607; A61B 2018/1455; A61B 2034/306; A61B 2018/0063
USPC ......... 227/175.1–182.1, 8, 19; 606/139, 142, 606/143, 205–208
See application file for complete search history.

(56) References Cited

U.S. PATENT DOCUMENTS

| | | | | |
|---|---|---|---|---|
| 5,389,098 | A * | 2/1995 | Tsuruta | A61B 17/07207 606/49 |
| 5,535,935 | A * | 7/1996 | Vidal | A61B 17/07207 227/176.1 |
| 5,632,432 | A * | 5/1997 | Schulze | A61B 17/07207 227/176.1 |
| 5,897,562 | A * | 4/1999 | Bolanos | A61B 17/07207 227/176.1 |
| 6,063,098 | A | 5/2000 | Houser et al. | |
| 7,494,039 | B2 | 2/2009 | Racenet et al. | |
| 7,909,220 | B2 | 3/2011 | Viola | |
| 8,241,322 | B2 | 8/2012 | Whitman | |
| 8,945,163 | B2 * | 2/2015 | Voegele | A61B 17/07207 227/180.1 |
| 9,414,855 | B1 * | 8/2016 | White | A61B 17/07207 |
| 11,317,917 | B2 | 5/2022 | Shelton, IV et al. | |
| 11,712,261 | B2 | 8/2023 | Hunter et al. | |
| 12,185,949 | B2 * | 1/2025 | Beardsley | A61B 17/072 |
| 2003/0114851 | A1 * | 6/2003 | Truckai | A61B 18/1445 606/205 |
| 2007/0114261 | A1 * | 5/2007 | Ortiz | A61B 17/07207 227/175.1 |
| 2007/0250113 | A1 | 10/2007 | Hegeman et al. | |
| 2009/0039137 | A1 * | 2/2009 | Viola | A61B 17/07207 227/176.1 |
| 2010/0016852 | A1 * | 1/2010 | Manzo | A61B 34/71 606/41 |
| 2010/0320252 | A1 | 12/2010 | Viola et al. | |
| 2011/0106078 | A1 | 5/2011 | Mueller | |
| 2011/0108606 | A1 * | 5/2011 | Whitman | A61B 17/068 227/180.1 |
| 2011/0248064 | A1 * | 10/2011 | Marczyk | A61B 17/07207 227/114 |
| 2015/0090759 | A1 | 4/2015 | Spivey et al. | |
| 2015/0313676 | A1 | 11/2015 | Deodhar | |
| 2016/0192996 | A1 * | 7/2016 | Spivey | A61B 1/00042 227/176.1 |
| 2016/0303745 | A1 | 10/2016 | Rockrohr | |
| 2019/0105032 | A1 * | 4/2019 | Crews | A61B 17/0469 |
| 2019/0105052 | A1 * | 4/2019 | Swayze | A61B 17/1155 |
| 2019/0128347 | A1 * | 5/2019 | Leimbach | A61B 34/71 |
| 2019/0239877 | A1 * | 8/2019 | Ragosta | A61B 34/71 |
| 2019/0290263 | A1 * | 9/2019 | Morgan | A61B 34/37 |
| 2019/0380735 | A1 | 12/2019 | Cuti et al. | |
| 2020/0093554 | A1 | 3/2020 | Schuh et al. | |
| 2020/0305868 | A1 | 10/2020 | Shelton, IV | |
| 2021/0052332 | A1 * | 2/2021 | Saulenas | A61B 17/2909 |
| 2021/0161531 | A1 * | 6/2021 | Sabaris Vilas | A61B 5/0261 |
| 2021/0196356 | A1 | 7/2021 | Shelton, IV et al. | |
| 2021/0401524 | A1 | 12/2021 | Suresh et al. | |
| 2022/0031350 | A1 | 2/2022 | Witte et al. | |
| 2022/0105638 | A1 | 4/2022 | Zhang et al. | |
| 2024/0299079 | A1 * | 9/2024 | Fischer | A61B 18/1445 |
| 2025/0025167 | A1 * | 1/2025 | Ryle | A61B 34/30 |
| 2025/0152169 | A1 * | 5/2025 | Hibner | A61B 17/320092 |
| 2025/0195070 | A1 * | 6/2025 | Lee | A61B 17/07207 |
| 2025/0261945 | A1 * | 8/2025 | Cabrera | A61B 17/1155 |

* cited by examiner 206
200
204
210
212
404
406
402
B 408b
206
408a
410
412
416
C
414
200
204
212
406

206
410
501
416
412
416
204
B
200

206
202
508b
410
508b
510
512
508a
506a
506b
204
B
200
508a
502
504

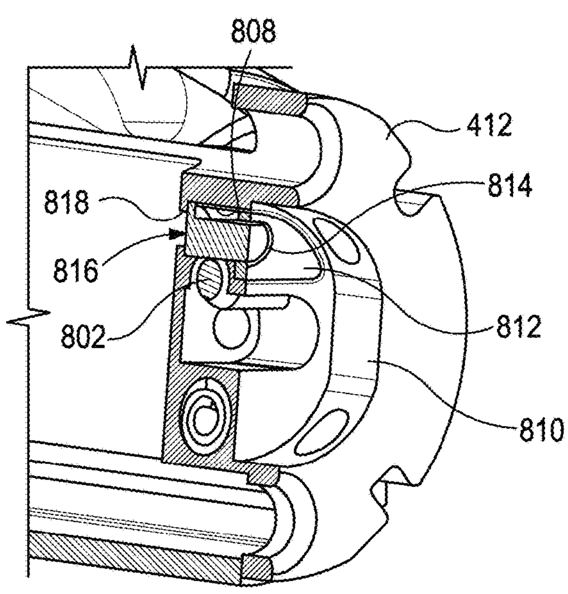
FIG. 8C
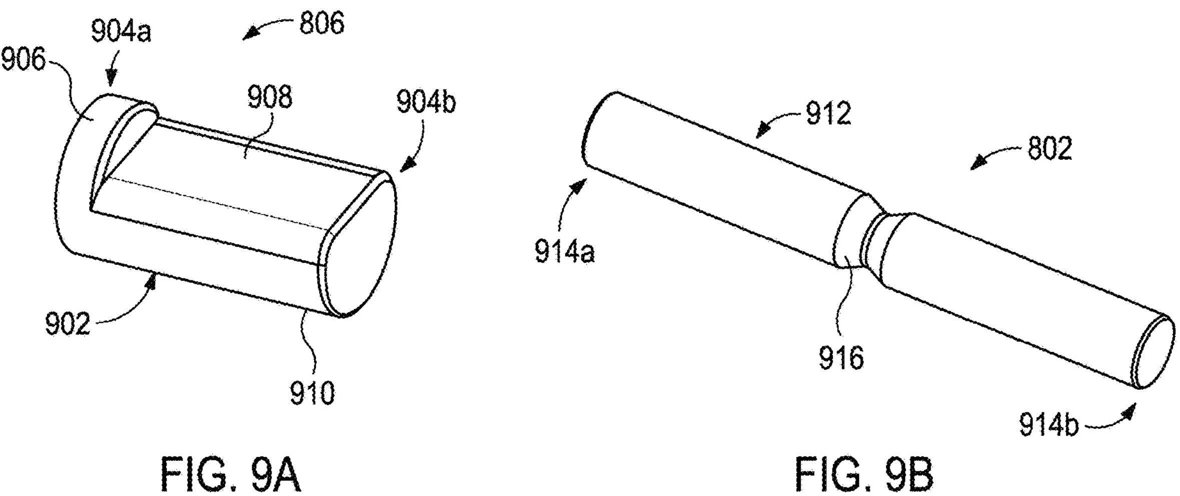
FIG. 9A
FIG. 9B
928
918
922a
920
922b
924
926
FIG. 9C

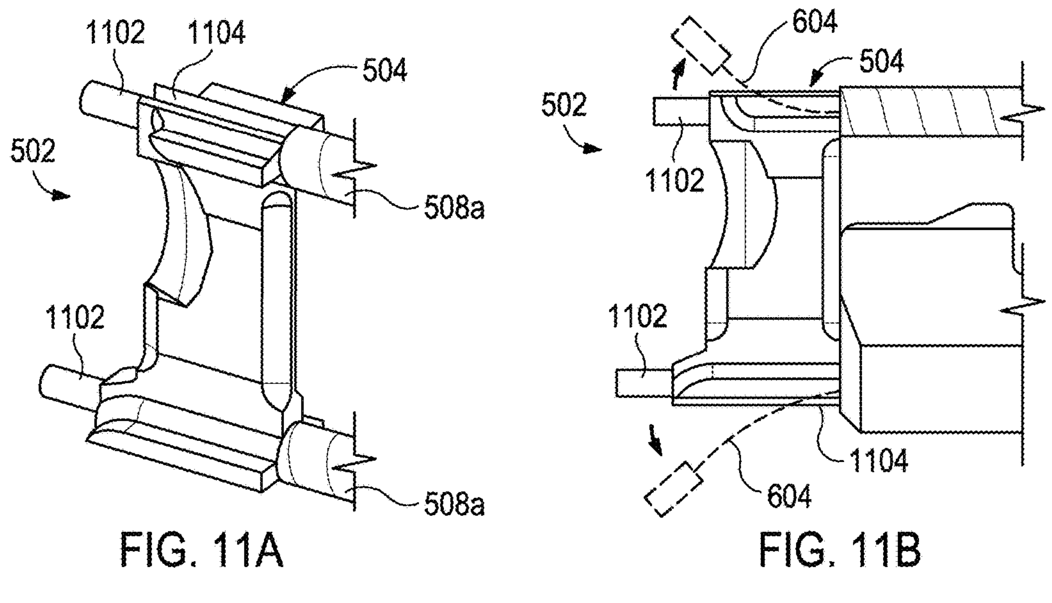
FIG. 11A
FIG. 11B
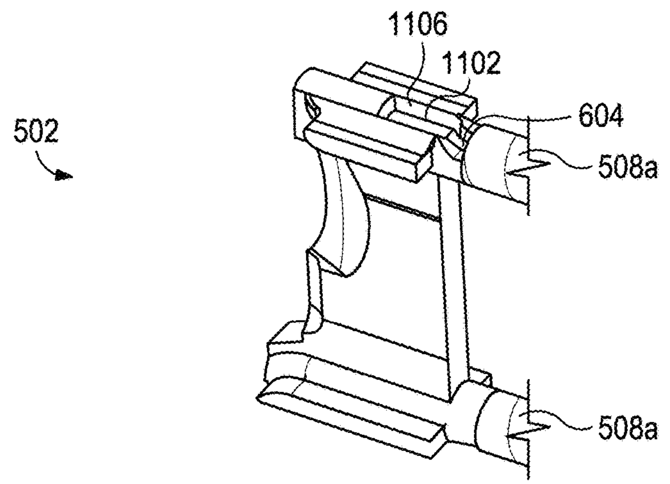
FIG. 12
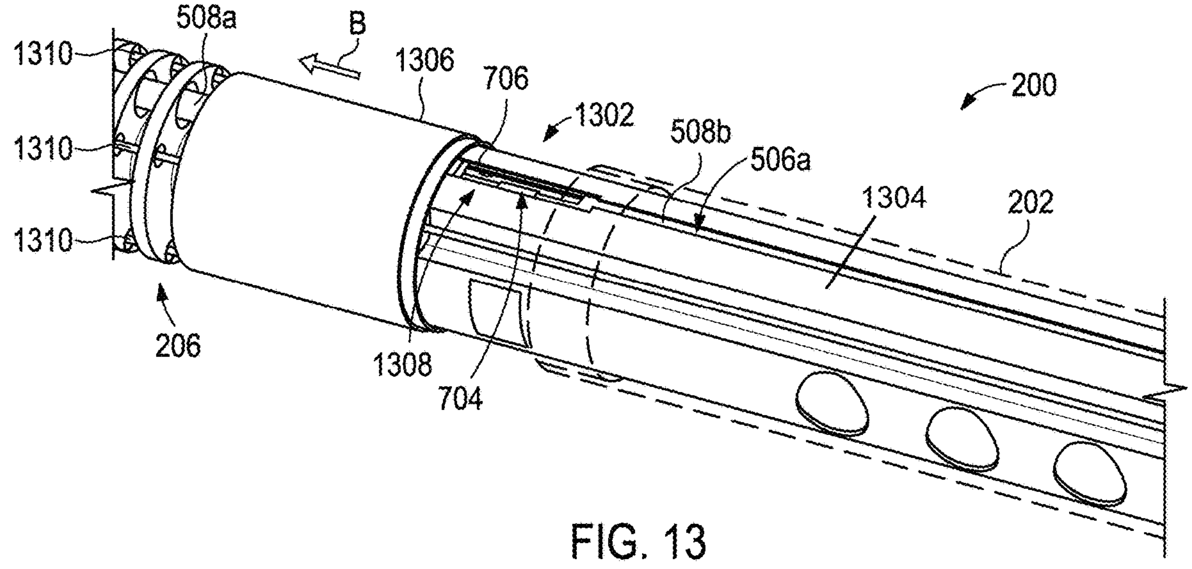
FIG. 13

CIRCULARITY SYSTEMS AND METHODS FOR SURGICAL STAPLERS

CROSS-REFERENCE TO RELATED APPLICATIONS

This application claims priority to and the benefit of U.S. Non-Provisional application Ser. No. 18/345,613 entitled "CIRCULARITY SYSTEMS AND METHODS FOR SURGICAL STAPLERS" filed on Jun. 30, 2023. The aforementioned application is incorporated by reference herein.

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system. Moving the drive cables articulates the end effector to desired angular positions and configurations.

MIS instruments incorporate various high-wear components that, over time, can mechanically or physically degrade and thereby limit the useful life of the instrument. Consequently, most MIS instruments are designed to be used only for a predetermined number of procedures, following which the instrument is often discarded. As can be appreciated, this can have an adverse impact on the environment.

In an effort to maintain the value of products, while simultaneously not creating additional environmental waste, companies and manufacturers are progressively looking for ways to incorporate "circularity" into their business model. Circularity is an economic model that follows the three "Rs": reuse, reprocess, and recycle, and aims to retain the lifespan of products through repair and maintenance, reusing, remanufacturing, or upcycling.

What is needed is a process or methodology of circularity concerning the reuse and recycling of MIS instruments, which minimizes the impact on the environment.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 8A-8C depict additional steps of disassembly, according to one or more additional embodiments of the present disclosure.

FIGS. 9A and 9B are isometric views of an example retention pin and an example anvil pin, respectively, according to one or more embodiments.

FIG. 9C is another example anvil pin, according to one or more embodiments.

FIGS. 11A and 11B are isometric and side views, respectively, of the distal end of the knife assembly showing example disassembly, according to one or more embodiments.

FIG. 12 is another isometric view of the distal end of the knife assembly, according to one or more additional embodiments.

FIG. 13 is an enlarged, isometric view of a portion of the distal end of the surgical tool depicting an alternative releasable connection, according to one or more embodiments.

DETAILED DESCRIPTION

The present disclosure is related to surgical tools and, more particularly, to prolonging the lifespan of surgical tools by implementing circularity systems and methods that result in replacement of one or more consumables included in the surgical tool.

The utilization or "lifespan" of a majority of robotic (and non-robotic) surgical tools is often limited due to the life or durability of just a few components within the surgical tool, referred to herein as "consumables". Embodiments disclosed herein describe how the design of the surgical tool can be modified to enable the consumable to be replaced rather easily, without requiring the surgical tool to be completely disassembled. Accordingly, the embodiments disclosed herein may prove advantageous in mitigating or entirely eliminating the need to scrap an entire surgical tool, but instead rehabilitate the used surgical tool by replacing one or more consumables.

Figure 1:
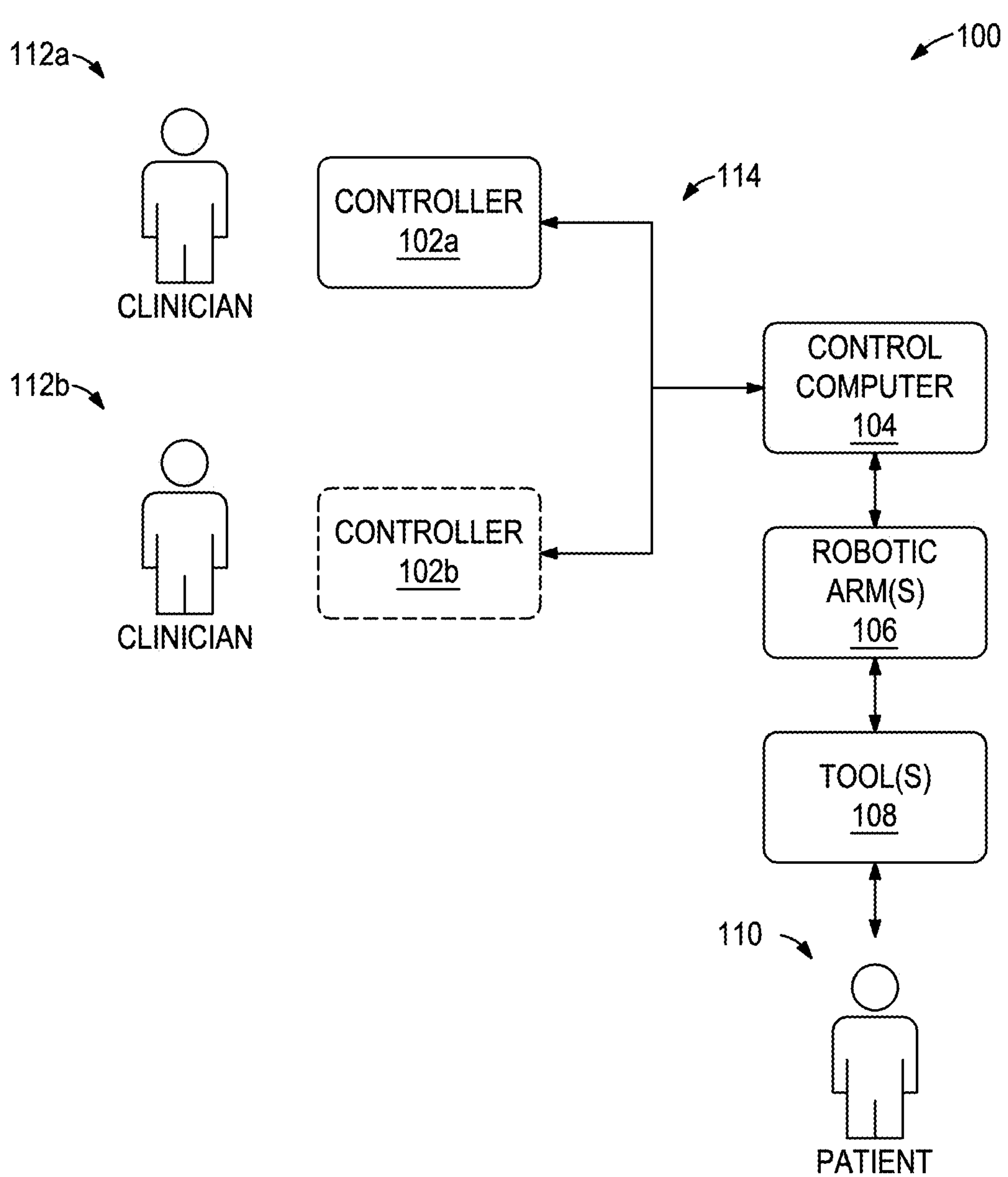
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102*a* and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112*a* (e.g., a surgeon) from the user input controller 102*a*.

In some embodiments, a second set of user input controllers 102*b* (shown in dashed line) may be operated by a second clinician 112*b* to direct operation of the robotic arms 106 and tools 108 via the control computer 104 and in conjunction with the first clinician 112*a*. In such embodiments, for example, each clinician 112*a,b* may control different robotic arms 106 or, in some cases, complete control of the robotic arms 106 may be passed between the clinicians 112*a,b* as needed. In some embodiments, additional robotic manipulators having additional robotic arms may be utilized during surgery on the patient 110, and these additional robotic arms may be controlled by one or more of the user input controllers 102*a,b*.

The control computer 104 and the user input controllers 102*a,b* may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102*a,b* generally include one or more physical controllers that can be grasped by the clinicians 112*a,b* and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws, applying an electrical potential (current) to an electrode, or the like. The control computer 104 can also include an optional feedback meter viewable by the clinicians 112*a,b* via a display to provide a visual indication of various surgical instrument metrics, such as the amount of force being applied to the surgical instrument (i.e., a cutting instrument or dynamic clamping member).

Figures 2, 3:
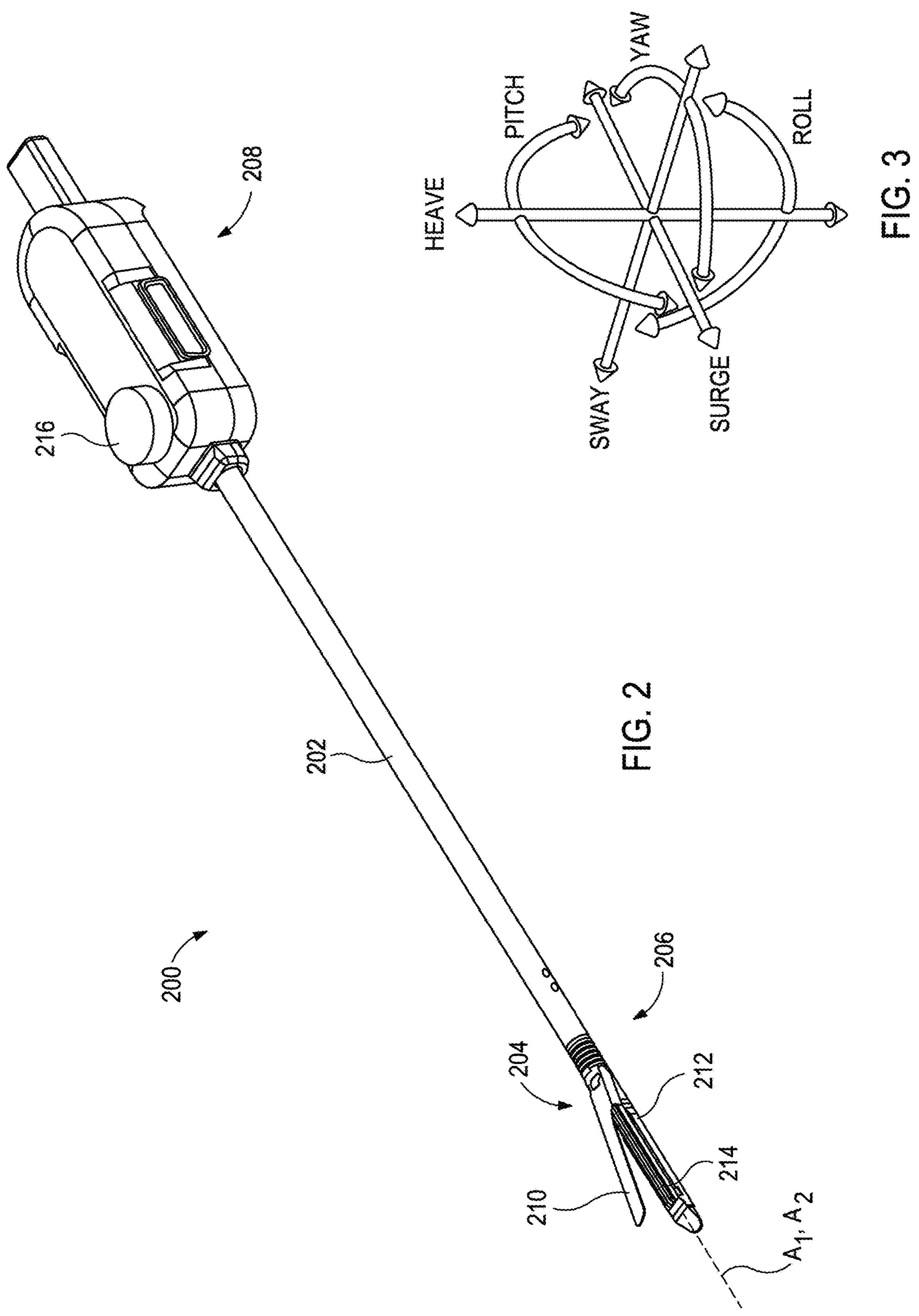
FIG. 2 is an isometric side view of an example surgical tool that may incorporate some or all of the principles of the present disclosure.
FIG. 3 illustrates potential degrees of freedom in which the wrist of the surgical tool of FIG. 2 may be able to articulate (pivot) and translate.

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the housing 208 includes (contains) various drive inputs and mechanisms (e.g., gears, actuators, etc.) designed to control operation of various features associated with the end effector 204 (e.g., clamping, firing, cutting, rotation, articulation, etc.). In at least some embodiments, the shaft 202, and hence the end effector 204 coupled thereto, is configured to rotate about a longitudinal axis $A_1$ of the shaft 202. In such embodiments, at least one of the drive inputs included in the housing 208 is configured to control rotational movement of the shaft 202 about the longitudinal axis $A_1$.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The end effector 204 can exhibit a variety of sizes, shapes, and configurations. In the illustrated embodiment, the end effector 204 comprises a surgical stapler, alternately referred to as an "endocutter," configured to cut and staple (fasten) tissue. As illustrated, the end effector 204 includes opposing jaws 210, 212 configured to move (articulate) between open and closed positions. The opposing jaws 210, 212, however, may alternately form part of other types of end effectors with jaws such as, but not limited to, a tissue grasper, surgical scissors, an advanced energy vessel sealer, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot to actuate the end effector 204 between the open and closed positions.

In the illustrated embodiment, the first jaw 210 may be characterized or otherwise referred to as an "anvil" jaw, and the second jaw 212 may be characterized or otherwise referred to as a "cartridge" jaw. More specifically, the second jaw 212 may include a frame that houses or supports a staple cartridge, and the first jaw 210 is pivotally supported relative to the second jaw 212 and defines a surface that operates as an anvil to form staples ejected from the staple cartridge during operation. In use, the first jaw 210 is rotatable between an open, unclamped position and a closed, clamped position. In other embodiments, however, the second jaw 212 may move (rotate) relative to the second jaw 210, without departing from the scope of the disclosure.

FIG. 3 illustrates the potential degrees of freedom in which the wrist 206 may be able to articulate (pivot) and thereby move the end effector 204. The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of the end effector 204 with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate actuation and articulation of the end effector 204 relative to the shaft 202. Moving (actuating) one or more of the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

Other drive members may extend to the end effector 204, and selective actuation of those drive members may cause the end effector 204 to actuate (operate). In the illustrated embodiment, actuating the end effector 204 may comprise closing and/or opening the first jaw 210 relative to the second jaw 212 (or vice versa), thereby enabling the end effector 204 to grasp (clamp) onto tissue. In addition, once tissue is grasped or clamped between the opposing jaws 210, 212, actuating the end effector 204 may further comprise "firing" the end effector 204, which may refer to causing a cutting element or knife (not visible) to advance distally within a slot 214 defined in the second jaw 212. As it moves distally, the cutting element may transect any tissue grasped between the opposing jaws 210, 212. Moreover, as the cutting element advances distally, a plurality of staples contained within the staple cartridge (i.e., housed within the second jaw 212) may be urged (cammed) into deforming contact with corresponding anvil surfaces (e.g., pockets) provided on the first jaw 210. The deployed staples may form multiple rows of staples that seal opposing sides of the transected tissue.

In some embodiments, the surgical tool 200 may be configured to apply energy to tissue, such as radio frequency (RF) energy. In such cases, actuating the end effector 204 may further include applying energy to tissue grasped or clamped between the opposing jaws 210, 212 to cauterize or seal the captured tissue, following which the tissue may be transected.

In some embodiments, the surgical tool 200 may further include a manual closure device 216 accessible to a user on the exterior of the drive housing 208. As illustrated, the manual closure device 216 may comprise a rotatable knob that may be grasped by the user. The manual closure device 216 may be operatively coupled to various gears and/or drive members within the drive housing 208 to allow a clinician to manually open and close the jaws 210, 212. In some cases, a clinician may be able to fully clamp and fully unclamp the jaws 210, 212 by manipulating the manual closure device 216. The manual closure device 216 may be particularly useful to a clinician when the surgical tool 200 is detached from a surgical robot, since having the capability to open and close the jaws 210, 212 may eliminate the need to place inadvertent stress on internal drive members or components. In the event that a clinician desires to manually open the jaws 210, 212 when the surgical tool 200 is still attached to a surgical robot, the clinician can rotate the manual closure device 216 in an attempt to open the end effector 204.

Similar to most surgical tools, the surgical tool 200 includes various high-wear components, referred to herein as "consumables," that, over time, can mechanically or physically degrade and thereby limit the useful life of the surgical tool 200. Consequently, the surgical tool 200 may be designed to be used for only a predetermined number of procedures. Once the predetermined number of procedures is reached, the operator (e.g., a nurse, a doctor, etc.) may be unable to continue using the surgical tool 200. In such cases, the surgical tool 200 would conventionally be discarded, which can have an adverse impact on the environment.

According to embodiments of the present disclosure, instead of discarding the surgical tool 200, the surgical tool 200 may be subject to circularity processing or a circular economy model or approach designed to reprocess and recycle the surgical tool 200 for further use. In circularity processing, the surgical tool 200 is decommissioned upon reaching the predetermined number of procedures, and then subsequently sent to a service center where trained technicians clean and mount the surgical tool 200 to a disassembly fixture. While mounted to the disassembly fixture, various portions of the surgical tool 200 may be disassembled to access and remove one or more consumables forming part of the surgical tool 200. The removed consumables can then be cleaned and refurbished or replaced with new consumables. The surgical tool 200 may then be reassembled, cleaned, tested, delivered to a distribution center, and subsequently sent to an end user (e.g., a hospital, a surgeon, an operator, etc.) for further use.

Figures 4A, 4B:
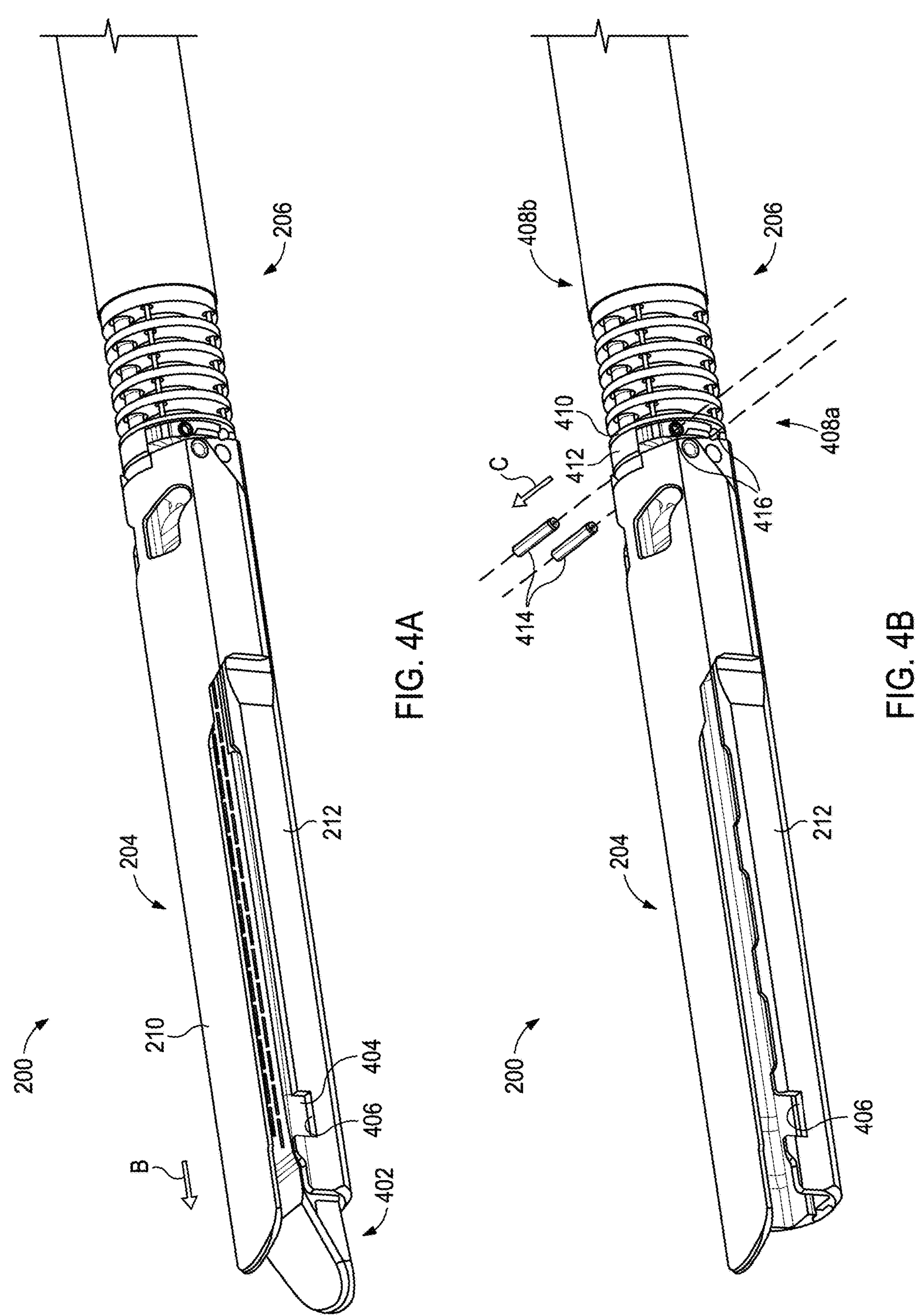
FIGS. 4A and 4B are enlarged isometric views of the distal end of the surgical tool, according to one or more embodiments.

FIGS. 4A and 4B are enlarged isometric views of the distal end of the surgical tool 200, according to one or more embodiments. More specifically, FIGS. 4A-4B are enlarged views of the end effector 204 and the wrist 206 showing progressive disassembly of the distal portion(s) of the surgical tool 200. To be able to access the various "consumables" of the surgical tool 200, the surgical tool 200 may be subject to a surgical tool circularity process or procedure, which is designed to progressively disassemble portions of the surgical tool 200 to access such consumables. Consistent with such circularity processes or procedures, in some embodiments, the surgical tool 200 may be secured to a disassembly fixture (not shown) configured to receive and mount the surgical tool 200. The disassembly fixture may be provided at a service center that employs technicians trained to clean, disassemble, and refurbish the surgical tool 200, as described herein. In such embodiments, the disassembly fixture provides features or structural components capable of mounting the drive housing 208 at one end and simultaneously supporting the end effector 204 and the wrist 206 at the opposing end. Once the surgical tool 200 is properly secured to the disassembly fixture, the following steps of disassembling the surgical tool 200 described herein below may be undertaken to access and replace (or refurbish) the consumables forming part of the surgical tool 200.

Referring first to FIG. 4A, the jaws 210, 212 are shown in the closed position, and the lower jaw 212 of the end effector 204 includes a staple cartridge 402 removably mounted thereto. As briefly mentioned above, the end effector 204 is actuated or "fired" by first closing the first jaw 210 relative to the second jaw 212 and thereby capturing tissue between the two jaws 210, 212. Once tissue is grasped or clamped between the opposing jaws 210, 212, a cutting element or knife (not visible) is advanced distally within the slot 214 (FIG. 2) defined in the second jaw 212 and, more particularly, in the staple cartridge 402. As it moves distally, the knife transects the tissue grasped between the jaws 210, 212 and simultaneously and progressively urges a plurality of staples contained within the staple cartridge 402 against to the upper jaw 210, which operates as an "anvil" that deforms the staples. The resulting deployed staples can provide multiple rows of staples that seal opposing sides of the transected tissue.

The staple cartridge 402 may be removably attached to the lower jaw 212 via a variety of mechanisms and/or mechanical attachments. In some embodiments, for example, the staple cartridge 402 may include opposing spring-loaded tabs 404 configured to locate and be received within corresponding slots 406 defined in the lower jaw 212. In such embodiments, the staple cartridge 402 may be removed from the lower jaw 212 by manually retracting the spring-loaded tabs 404, and thereby de-coupling the spring-loaded tabs 404 from the corresponding slots 406. In other embodiments, however, the disassembly fixture described above could include a mechanical or robotic device operable to engage and retract the spring-loaded tabs 404 from the corresponding slots 406, without departing from the scope of the disclosure. The detached staple cartridge 402 may then be removed from the lower jaw 212 by moving the staple cartridge 402 in the distal direction B, In FIG. 4B, the staple cartridge 402 is removed from the lower jaw 212. The wrist 206 includes a first or "distal" end 408*a* and a second or "proximal" end 408*b* opposite the distal end 408*a*. At the distal end 408*b*, the wrist 206 includes a concentric disc mount 410 that may be at least partially received within and otherwise operatively coupled to a concentric disc receiver 412 arranged at the proximal end of the end effector 204. Securing the disc mount 410 to the disc receiver 412 operatively couples the wrist 206 to the end effector 204. In at least one embodiment, the disc mount 410 may be secured to the disc receiver 412 by extending one or more pins 414 laterally through axially overlapping and concentric portions of the mount 410 and the receiver 412. In the illustrated embodiment, two pins 414 are used, and each pin 414 may be received within corresponding apertures 416 defined in and extending laterally through aligned portions of both of the mount 410 and the receiver 412.

In some embodiments, the pins 414 may comprise spring pins or the like. In such embodiments, once received within the corresponding apertures 416, the spring pins 414 may form an interference fit within the apertures 416, thereby preventing removal of the pins 414 from the apertures 416. In other embodiments, however, the pins 414 may comprise other types of fastening mechanisms, such as a threaded fastener, where the pins 414 may be threaded into the apertures 416, without departing from the scope of the disclosure.

To uncouple and otherwise detach the end effector 204 from the wrist 206, the pins 414 may be removed from the apertures 416 by moving (sliding) the pins 414 out of the apertures 416 in the lateral direction C. In embodiments where the pins 414 comprise spring pins, this can be accomplished by forcing the pins 414 out of the apertures 416 with a tool sized to be received within the apertures 416. In at least one embodiment, the lateral direction C may be substantially perpendicular to the longitudinal axis $A_2$ (FIG. 2) of the end effector 204, but could be angularly offset from the longitudinal axis $A_2$ by other magnitudes, without departing from the scope of the disclosure.

Figures 5A, 5B:
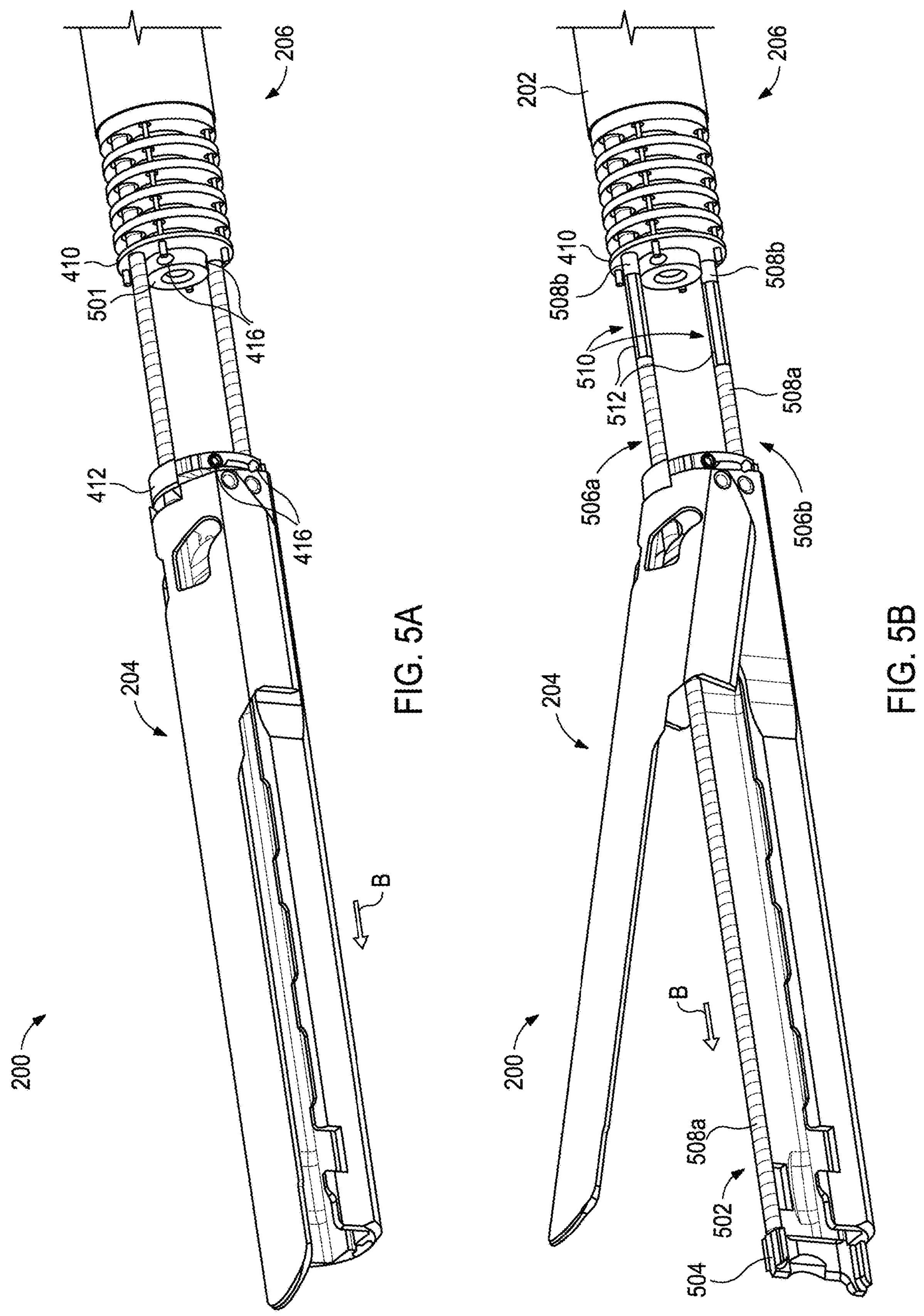
FIGS. 5A-5B are enlarged isometric views of the distal end of the surgical tool showing additional progressive steps of disassembly, according to one or more embodiments.

FIGS. 5A and 5B are enlarged isometric views of the distal end of the surgical tool 200 showing additional progressive steps of disassembly, according to one or more embodiments. More specifically, FIGS. 5A-5B depict enlarged, isometric views of the end effector 204 separated from the wrist 206. Referring first to FIG. 5A, once the pins 414 (FIG. 4B) are removed from the corresponding apertures 416, the end effector 204 can be separated from the wrist 206 in the distal direction B while the wrist 206 remains entirely intact. More specifically, removing the pins 414 allows the disc receiver 412 to be separated from the disc mount 410. As illustrated, the apertures 416 are defined in both the mount 410 and the receiver 412, and when the mount 410 is properly received within the receiver 412, the apertures 416 co-axially align to receive the pins 414. In at least one embodiment, the mount 410 may provide or otherwise define a protrusion 501 sized to be receive within a pocket (not visible) defined by the receiver 412.

In FIG. 5B, once the end effector 204 is moved distally from the wrist 206, a knife assembly 502 may be moved distally B and otherwise "hyper-advanced" relative to the disc mount 410. As illustrated, the knife assembly 502 includes a knife 504 operatively coupled to first and second drive members 506*a* and 506*b*. The drive members 506*a,b* extend from the drive housing 208 (FIG. 2) on angularly opposite sides of the shaft 202 and through the wrist 206. The drive members 506*a,b* form part of the actuation system housed within the drive housing 208, and may comprise bands, elongate members, belts, shafts, flexible shafts, drive rods, or any combination thereof. In some embodiments, the knife assembly 502 may be manually moved (hyper-advanced) in the distal direction B. This can be accomplished by manually moving (rotating) one or more drive inputs rotatably mounted to the bottom of the drive housing 208 and associated with advancing or retracting the knife assembly 502. In other embodiments, however, a robotic manipulator may be secured to the bottom of the drive housing 208 and operated to robotically actuate the drive input(s) associated with the knife assembly 502.

In the illustrated embodiment, each drive member 506*a,b* includes a distal section 508*a* and a proximal section 508*b* operatively and releasably coupled to the distal section 508*a*. The distal sections 508*a* terminate at and are operatively coupled to the knife 504, and the proximal sections 508*c* extend to the drive housing 208 (FIG. 2). Each distal section 508*a* may comprise, for example, a coil cable or the like, and each proximal section 508*b* may comprise a drive rod or the like. The distal and proximal sections 508*a,b* may be made of a material that is flexible but rigid enough to be able to drive the knife 504 distally and proximally during "firing" of the end effector 204. In particular, the distal and proximal sections 508*a,b* can be made from materials including, but not limited to, a metal (e.g., tungsten, stainless steel, nitinol, etc.), a polymer (e.g., ultra-high molecular weight polyethylene), a synthetic fiber (e.g., KEVLAR®, VECTRAN®, etc.), an elastomer, or any combination thereof.

The knife assembly 502 may be advanced distally B (hyper-extended) until exposing a releasable connection 510 between the distal and proximal sections 508*a,b* of each drive member 506*a,b*. The releasable connection 510 may prove advantageous in allowing a user (e.g., a technician) to decouple the distal and proximal sections 508*a,b*, thereby allowing the user to entirely separate or remove the end effector 204 from proximal portions of the surgical tool 200.

In the illustrated embodiment, the releasable connection 510 includes a knife drive spacer 512 axially interposing and releasably coupling the distal and proximal sections 508*a,b* of each drive member 506*a,b*. In some embodiments, the distal end of each knife drive spacer 512 may be fixedly attached to the corresponding distal section 508*a*, while the proximal end of each knife drive spacer 512 may be releasably or removably coupled to the corresponding proximal section 508*b*. In other embodiments, however, the knife drive spacer 512 may be fixedly attached to the proximal section 508*b* while releasably coupled to the distal section 508*a*, without departing from the scope of the disclosure.

Figure 6A:
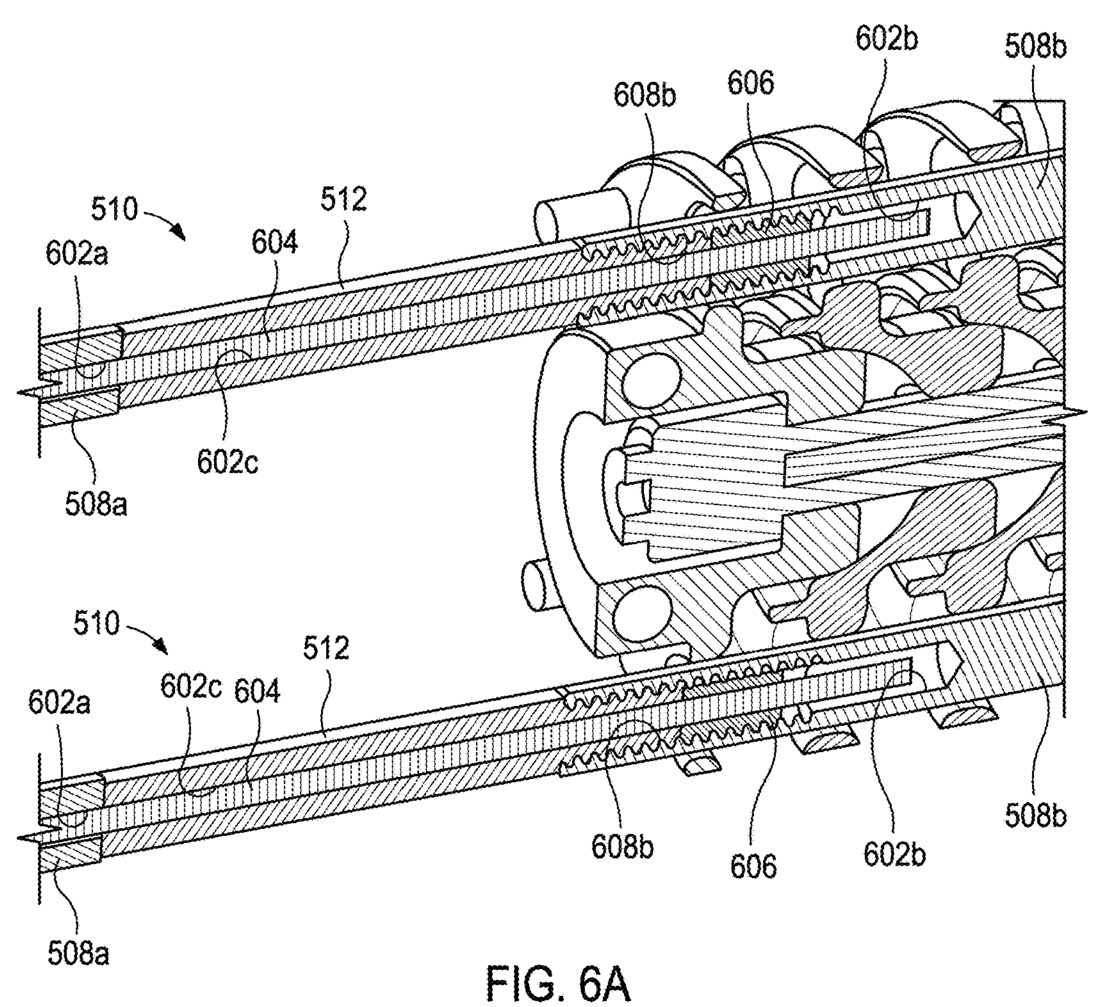
FIG. 6A is an enlarged cross-sectional side view of the releasable connection of FIG. 5B, according to one or more embodiments.
Figure 6B:
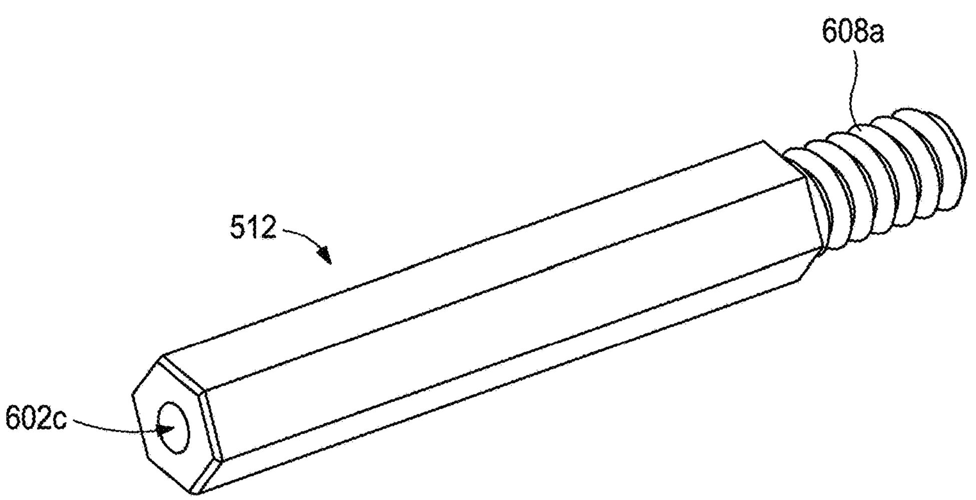
FIG. 6B is an isometric side view of one example of the knife drive spacer of the releasable connection of FIG. 5B, according to one or more embodiments.

FIG. 6A is an enlarged cross-sectional side view of the releasable connection 510 of FIG. 5B, and FIG. 6B is an isometric side view of one example of the knife drive spacer 512, according to one or more embodiments. As illustrated, the distal and proximal sections 508*a,b* and the knife drive spacer 512 each define an inner channel 602*a*, 602*b*, and 602*c*, and the inner channels 602*a-c* are configured to axially align to receive a cable 604 therein. The cable 604 extends within the inner channels 602*a,c* of the distal section 508*a* and the knife drive spacer 512, and terminates within the inner channel 602*b* of the proximal section 508*b*. The cable 604 may comprise, for example, a flexible material such as, but not limited to, a metal (e.g., tungsten, stainless steel, nitinol, etc.), a polymer (e.g., ultra-high molecular weight polyethylene), a synthetic fiber (e.g., KEVLAR®, VECTRAN®, etc.), an elastomer, or any combination thereof.

In some embodiments, the cable 604 may be fixedly attached to the distal section 508*a*, such as via a crimped engagement or an interference fit. Moreover, the cable 604 may be secured to the knife drive spacer 512 using one or more crimps 606, and a short length of the cable 604 may extend past the crimp 606 and into the adjacent inner channel 602*b* of the corresponding proximal section 508*b*. As illustrated, the knife drive spacer 512 may be removably coupled to the proximal section 508*b* via a threaded engagement, where external threading 608*a* (FIG. 6B) defined on the knife drive spacer 512 is configured to be threadably received by internal threading 608*b* defined on the inner channel 602*b* or interior of the proximal section 508*b*. Those skilled in the art, however, will readily appreciate that the knife drive spacer 512 may be removably coupled to the proximal section 508*b* via other removable or detachable means or mechanisms, without departing from the scope of the disclosure. Once the releasable connection 510 is disengaged (e.g., the knife drive spacer 512 is decoupled from the proximal section 508*b*) the end effector 204 may be entirely separated and removed from proximal portions of the surgical tool 200.

Figure 7A:
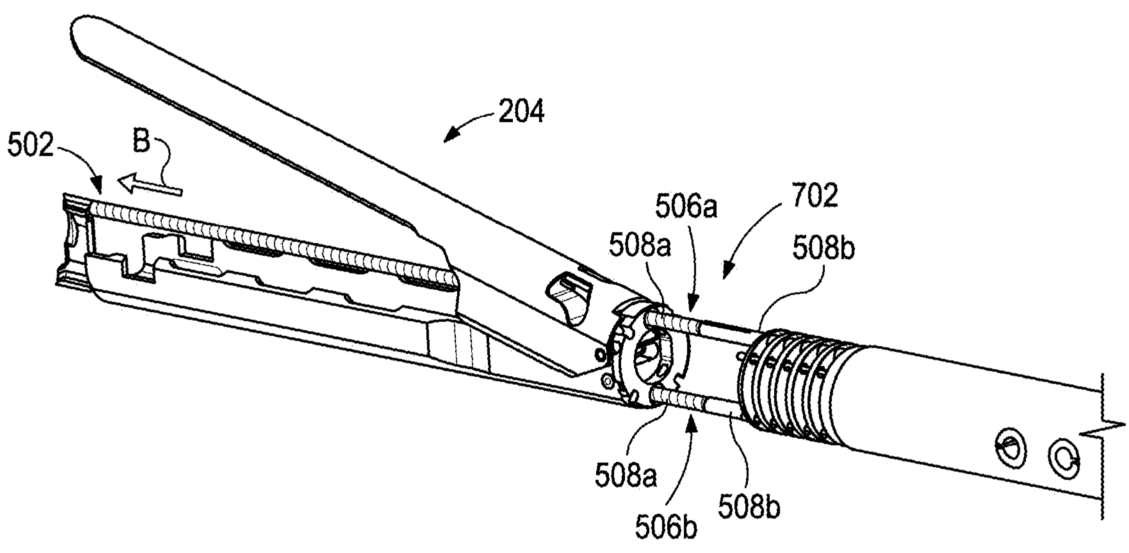
FIGS. 7A and 7B are isometric and enlarged isometric views, respectively, of an alternative example of a releasable connection, according to one or more additional embodiments.
Figure 7B:
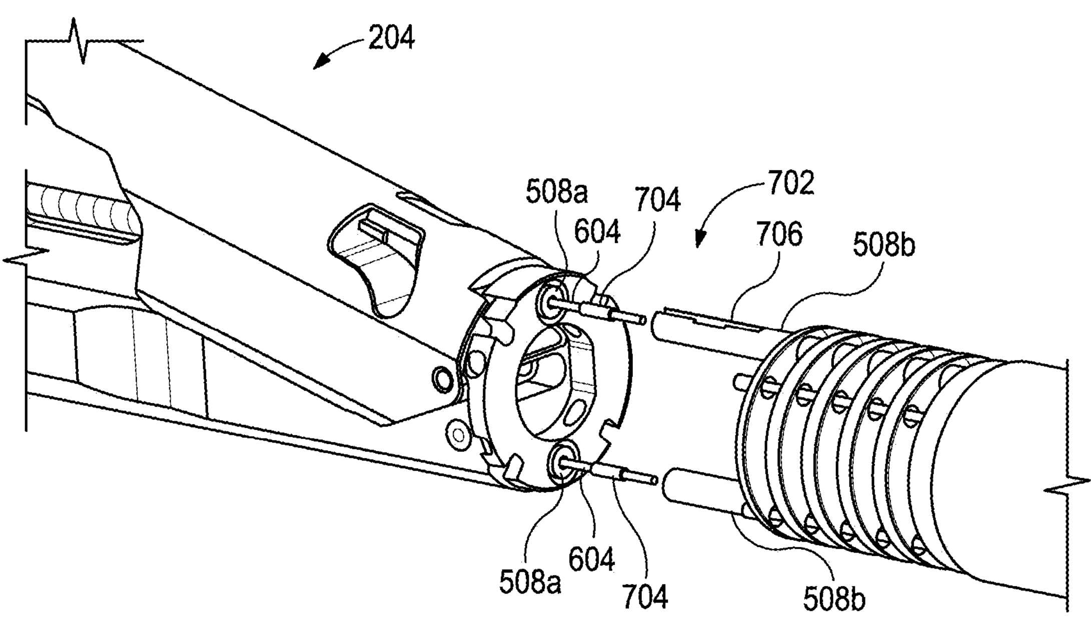

FIGS. 7A and 7B are isometric and enlarged isometric views, respectively, of an alternative example of a releasable connection 702, according to one or more additional embodiments. The releasable connection 702 may be similar in some respects to the releasable connection 510 of FIG. 5B, and therefore may be best understood with reference thereto. Similar to the releasable connection 510, for example, the releasable connection 702 releasably couples the distal and proximal sections 508*a,b* of each drive member 506*a,b*. Moreover, the knife assembly 702 needs to be advanced distally B (hyper-advanced) until exposing the releasable connection 702.

Referring to FIG. 7B, in the illustrated embodiment, the releasable connection 702 for each drive member 506*a,b* includes a crimp 704 fixedly attached to the corresponding cable 604 extending within the distal section 508*a*. Moreover, each crimp 704 is sized and otherwise configured to be received within a corresponding pocket 706 (one visible) defined in each proximal section 508*b*. Once properly received within the corresponding pocket 706 the crimp 704 effectively couples the distal and proximal sections 508*a,b*. In contrast, once the crimps 704 are disengaged from (e.g., lifted up and out of) the corresponding pocket 706, the end effector 204 may be entirely separated and removed from proximal portions of the surgical tool 200.

Figure 8A:
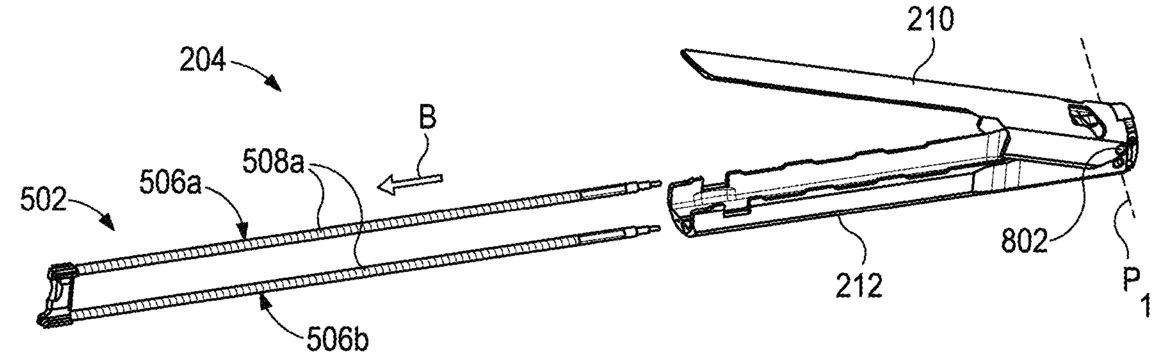
Figure 8B:
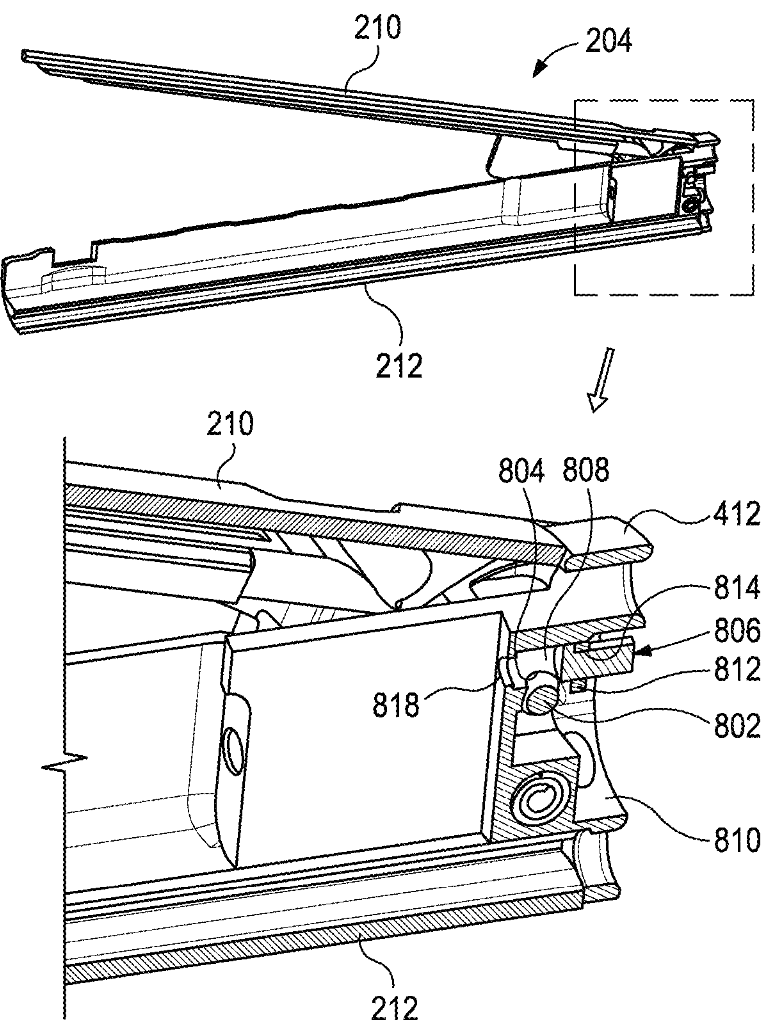

FIGS. 8A and 8B depict additional steps of disassembly, according to the present disclosure. More specifically, FIGS. 8A-8B depict further disassembly of the end effector 204. Referring first to FIG. 8A, once the distal sections 508*a* of each drive member 506*a* are properly disengaged from the corresponding proximal sections 508*b* (FIGS. 5B and 7A-7B), as generally described above, the knife assembly 502 can be separated from the upper and lower jaws 210, 212 by moving (translating) the knife assembly 502 in the distal direction B.

The end effector 204 is further disassembled by uncoupling (detaching) the upper jaw 210 from the lower jaw 212. The upper jaw 210 is pivotably coupled to the lower jaw 212 with an anvil pin 802. The anvil pin 802 extends through coaxially alignable apertures defined in both the upper and lower jaws 210, 212 and is pivotable about a pivot axis $P_1$ that is substantially perpendicular to the longitudinal axis $A_2$ (FIG. 2) of the end effector 204. Removing the anvil pin 802 will allow the upper jaw 210 to be detached (separated) from the lower jaw 212.

FIG. 8B is a cross-sectional side view of the upper and lower jaws 210, 212, including an enlarged inset graphic showing the pivotable connection between the upper and lower jaws 210, 212. More specifically, as illustrated, the disc receiver 412 is arranged at the proximal ends of the upper and lower jaws 210, 212 and extends distally into an internal cavity defined by the lower jaw 212. Moreover, the anvil pin 802 extends laterally through an aperture 804 defined in the disc receiver 412. As discussed below, the aperture 804 is coaxial with apertures defined in both the upper and lower jaws 210, 212 to receive the anvil pin 802.

The disc receiver 412 further includes a retention pin 806 axially movable within a pin slot 808 between a first or "engaged" position and a second or "disengaged" position. When in the engaged position, the retention pin 806 engages the anvil pin 802 and thereby prevents the anvil pin 802 from moving laterally within the aperture 804 and otherwise securing the anvil pin 802 from removal. In contrast, when moved to the disengaged position, the retention pin 806 is moved out of engagement with the anvil pin 802, thereby allowing the anvil pin 802 to exit the aperture 804 and be removed from the end effector 204, which allows the upper jaw 210 to be detached from the lower jaw 212.

Referring briefly to FIGS. 9A and 9B, illustrated are isometric views of an example retention pin 806 and an example anvil pin 802, respectively, according to one or more embodiments. In FIG. 9A, the retention pin 806 provides a generally cylindrical body 902 having a first end 904*a* and a second end 904*b* opposite the first end 904*a*. A radial shoulder 906 is provided at the first end 904*a* and a planar surface 908 extends from the radial shoulder 906. Opposite the planar surface 908, the body 902 provides a generally arcuate or curved surface 910. The radial shoulder 906 exhibits a diameter or size larger than the planar surface 908, and the radial shoulder 906 and the planar surface 908 cooperatively help to maintain the retention pin 806 within the pin slot 808 (FIG. 8B).

In FIG. 9B, the anvil pin 802 provides a generally cylindrical body 912 having a first end 914*a* and a second end 914*b* opposite the first and 914*a*. The body 912 exhibits a generally circular cross-section and includes a reduced diameter section or groove 916 provided and otherwise defined at or near a midpoint between the first and second ends 914*a,b*. The groove 916 may be configured to receive the retention pin 806 (FIG. 9A). More specifically, when the retention pin 806 is in the engaged position, the curved surface 910 of the retention pin 806 will be received within the groove 916, thereby preventing the anvil pin 802 from being removed laterally from the end effector 204 (FIGS. 8A-8B).

FIG. 9C is another example anvil pin 918, according to one or more additional embodiments. The anvil pin 918 may be similar in some respects to the anvil pin 802 of FIGS. 8B and 9B, and therefore may be best understood with reference thereto. Similar to the anvil pin 802, for example, the anvil pin 918 provides a cylindrical body 920 having opposing first and second ends 922*a* and 922*b*, and exhibiting a generally circular cross-section. Moreover, the body 902 includes a reduced diameter section or groove 924 defined at or near a midpoint between the first and second ends 922*a,b*. Similar to the groove 916 (FIG. 9B), the groove 924 may be configured to receive the retention pin 806 (FIG. 9A). More specifically, when the retention pin 806 is in the engaged position, the curved surface 910 (FIG. 9A) of the retention pin 806 will be received within the groove 924, thereby preventing the anvil pin 918 from rotating and unthreading from the end effector (FIGS. 8A-8B), thereby preventing the anvil pin 918 from being removed laterally from the end effector 204.

Unlike the anvil pin 802, however, the anvil pin 918 is able to be threaded to one or both of the upper and lower jaws 210, 212 (FIGS. 8A-8B). More specifically, as illustrated, the first end 922*a* of the anvil pin 918 may be threaded and otherwise define threading 926 capable of being threaded into corresponding threading defined on one or both of the upper and lower jaws 210, 212. The second end 922*b* of the anvil pin 918 may include an enlarged head 928, which is larger than the aperture(s) through which the anvil pin 918 is extended. Once extended through the coaxially aligned apertures defined in the upper and lower jaws and the disc receiver 412, the anvil pin 918 may be threaded to one side and the head 928 may secure the opposing side. The anvil pin 918 may prove advantageous in helping to prevent the side walls of the upper jaw 210, alternately referred to as the "anvil," from flaring radially outward when the jaws 210, 212 are closed and grasp onto tissue.

Referring again to FIG. 8B, with additional reference to FIG. 8C, example disassembly of the anvil pin 802 will now be provided. As illustrated, the disc receiver 412 provides and otherwise defines a central pocket 810. The central pocket 810 may be sized and otherwise configured to receive a corresponding protrusion provided by the disc mount 410 (FIGS. 4A and 5A-5B). In FIG. 8B, the retention pin 806 is shown in the disengaged position, and the retention pin 806 extends partially into the central pocket 810. In contrast, in FIG. 8C, the retention pin 806 is shown in the engaged position, and the retention pin 806 is fully received within the pin slot 808. When the disc mount 410 is operatively coupled to the disc receiver 412 and properly received within the central pocket 810, the retention pin 806 is forced distally into the pin slot 808, which secures the anvil pin 802 in place. Accordingly, the retention pin 806 cannot be moved to the disengaged position unless the disc mount 410 is first removed from the disc receiver 412.

As illustrated, the retention pin 806 is at least partially retained within the pin slot 808 with a cap plate 812. The cap plate 812 may be secured within the central pocket 810 and otherwise at an opening to the pin slot 808. In at least one embodiment, the cap plate 812 is welded to the central pocket 810, but could alternatively be secured within the pocket 810 via other fastening means. Moreover, the cap plate 812 defines an aperture 814 sized to receive the cross-sectional shape of the retention pin 806 corresponding to the planar surface 908 (FIG. 9A). The radial shoulder 906 (FIG. 9A) provided on the retention pin 806 prevents the retention pin 806 from fully extending through the aperture 814, thus retaining the retention pin 806 within the pin slot 808.

When the retention pin 806 is in the engaged position, as shown in FIG. 8C, the retention pin 806 is received within the groove 916 (FIG. 9B) of the anvil pin 802 (or the groove 924 of the anvil pin 918 of FIG. 9C). As mentioned above, this prevents the anvil pin 802 from dislodging or otherwise being removed from the end effector 204. To move the retention pin 806 from the engaged position to the disengaged position, as shown in FIG. 8B, the retention pin 806 must be moved proximally within the pin slot 808 (to the right in FIGS. 8B-8C). This may be accomplished by manually accessing the pin slot 808 via a slot aperture 818 defined at the distal end of the pin slot 808. More particularly, a user (e.g., a technician) may manually extend an elongate tool or rod (not shown) through the slot aperture 818 until engaging the distal end 904*a* (FIG. 9A) of the retention pin 806. The retention pin 806 may then be manually pushed and otherwise translated proximally within the pin slot 808 until moved to the disengaged position and otherwise out of engagement with the anvil pin 802.

Figure 10:
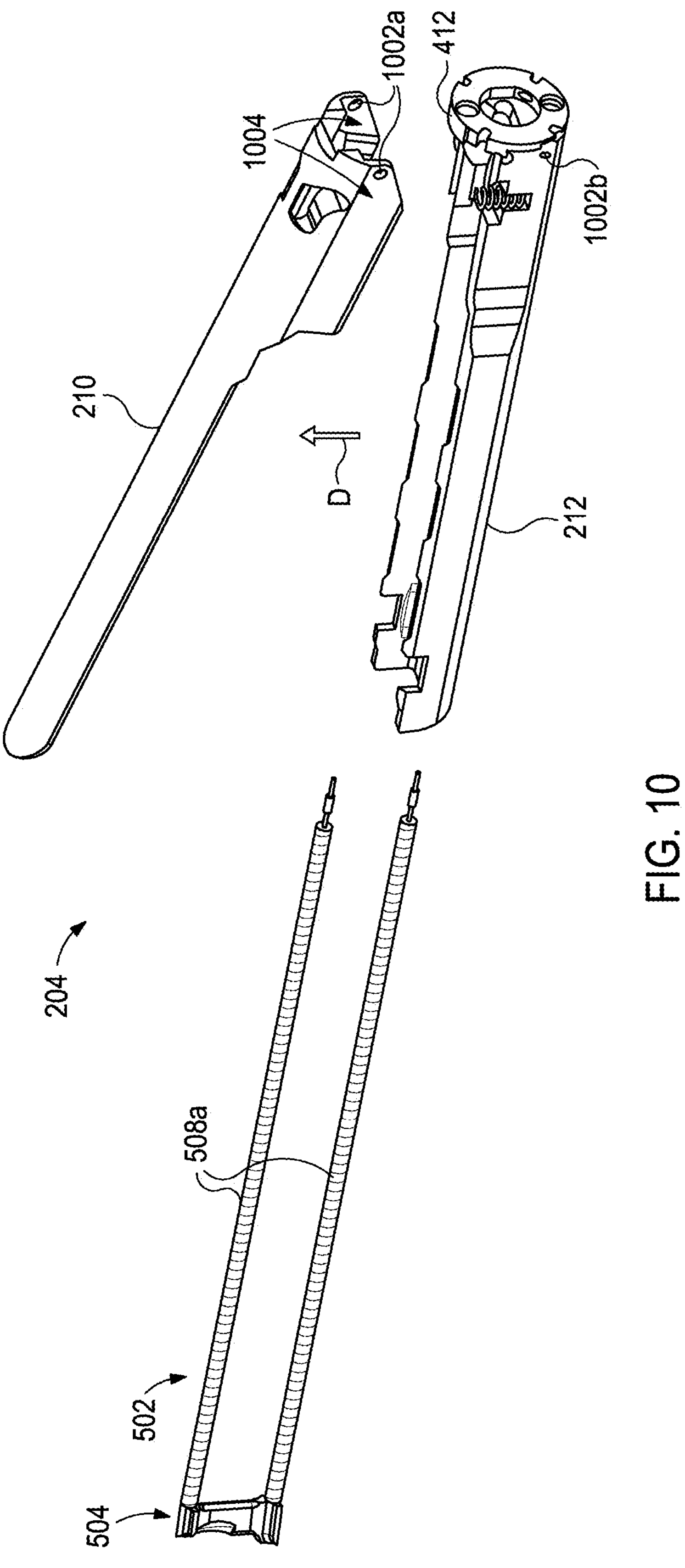
FIG. 10 is an exploded, isometric view of the end effector, according to one or more embodiments.

FIG. 10 is an exploded, isometric view of the end effector 204, according to one or more embodiments. Once the anvil pin 802 (FIGS. 8B-8C and 9B) is removed, the upper jaw 210 or "anvil" can be removed from the lower jaw 212 by moving the upper jaw 210 vertically, as shown by the arrow the D. As illustrated, the upper jaw defines sidewall apertures 1002*a* and the lower jaw defines sidewall apertures 1002*b* (only one visible) that coaxially align with the aperture 804 (FIG. 8B) defined in the disc receiver 412 when the upper jaw 210 is properly mounted to the lower jaw 212. In embodiments that use the anvil pin 918 of FIG. 9C, the anvil pin 918 may be threaded into one or both of the sidewall apertures 1002*a,b*, but at least to the sidewall aperture 1002*a* of the upper jaw 210. Accordingly, at least one or more of the sidewall apertures 1002*a* of the upper jaw 210 may be threaded and otherwise capable of receiving the threading 926 (FIG. 9C) defined on the anvil pin 918. Once extended through the coaxially aligned apertures 804 and 1002*a,b*, the anvil pin 918 may be threaded to the sidewall aperture 1002*a* provided on one sidewall 1004 of the upper jaw 210, and the enlarged head 928 may be urged against the opposing sidewall 1004 when tightened. This may prove advantageous in helping to prevent the opposing side walls 1004 of the upper jaw 210 from flaring laterally outward when the jaws 210, 212 are closed and grasp onto tissue.

Portions of the end effector 204, such as the blade assembly 502, the anvil 210, and the lower jaw 212 may be each constitute individual "consumables" that may be replaced at this time. Moreover, in some embodiments, the blade assembly 502 may be further disassembled into smaller consumable component parts. More specifically, the knife 504 may be detached from the distal sections 508*a*, and the knife 504 and the distal sections 508*a* may be considered individual "consumables" that may be replaced or refurbished, if needed. Each of these consumable components may be considered high-wear components that have a shortened lifespan, and thus may need to be replaced periodically via the presently disclosed circularity processing system and method.

Referring to FIGS. 11A and 11B, illustrated are isometric and side views, respectively, of the distal end of the knife assembly 502 showing example disassembly, according to one or more embodiments. In the illustrated embodiment, each distal section 508*a* may terminate with a crimp 1102 secured to the distal end of the corresponding cable 604 (shown in dashed lines in FIG. 11B). The knife 504 may define or provide upper and lower open slots 1104 into which the cable 604 may be received, and upon placing tension on the cable 604 the crimps 1102 are secured against the available space distal from the knife 504.

As shown in FIG. 11B, the crimps 1102 may be disengaged from the knife 504 by providing slack to the cables 604 and removing the cables from the corresponding open slots 1104. Once the cables 604 are removed from the open slots 1104, the knife 504 will then be effectively detached from the distal sections 508*a*. The knife 504 and/or the distal sections 508*a* can then be replaced as "consumables" and a new knife and/or distal section(s) can be reassembled to form the knife assembly 502.

FIG. 12 is another isometric view of the distal end of the knife assembly 502, according to one or more additional embodiments. Similar to the knife assembly 502 of FIGS. 11A-11B, the crimps 1102 (only one visible) are secured to the distal end of the corresponding cable 604 extending within the interior of the distal sections 508*a*. Unlike the knife assembly 502 of FIGS. 11A-11B, however, the crimps 1102 are received within corresponding open slotted pockets 1106 defined at the top and bottom of the knife 504.

The foregoing steps of disassembly and detachment of the surgical tool 200 (FIG. 2) up to this point may then be reversed to place the surgical tool 200 back into service. In particular, in a process that reverses the process outlined in FIGS. 11A-11B or FIG. 12 above, the distal sections 508*a* can be operatively coupled to the knife 504, thereby providing a new or refurbished knife assembly 502.

Moreover, in a process that reverses the process outlined in FIGS. 8B-8C and 10, the upper jaw 210 or "anvil" can be re-engaged with the lower jaw 212, and the anvil pin 802 may be extended through the coaxially aligned apertures (including the aperture 804 defined in the disc receiver 412). Once the anvil pin 802 is properly received within the coaxially aligned apertures, the retention pin 806 may be moved to the engaged position, as shown in FIG. 8C, where the retention pin 806 is received within the groove 916, 924 (FIGS. 9B and 9C) of the anvil pin 802, 918 (FIGS. 9B and 9C). This prevents the anvil pin 802 from dislodging or otherwise being removed from the end effector 204. In at least one embodiment, this may occur when the disc mount 410 (FIGS. 4A and 5A-5B) is received by and coupled to the disc receiver 412.

In a process that reverses the process outlined in FIG. 8A above, the knife assembly 502 can be again received within the upper and lower jaws 210, 212.

In a process that reverses the process outlined in FIGS. 5A and 5B, the distal and proximal sections 508*a,b* of the drive members 506*a,b* can be reattached at corresponding releasable connections. More specifically, in embodiments where the releasable connection 510 of FIGS. 6A-6B is incorporated, the knife drive spacer 512 may be re-threaded into the distal end of the proximal sections 508*b*. In contrast, in embodiments where the releasable connection 702 of FIGS. 7A-7B is incorporated, the crimps 704 fixedly attached to the corresponding cable 604 may be received within the corresponding pockets 706 defined in each proximal section 508*b*.

In a process that reverses the process outlined in FIG. 4B, the disc mount 410 is received by the disc receiver 412. The pins 414 are then received within the apertures 416 to secure the disc mount 410 to the disc receiver 412. This operatively couples the end effector 204 to the wrist 206. Moreover, in a process that reverses the process outlined in FIGS. 4A, the staple cartridge 402 may be re-attached to the lower jaw 212.

Finally, the surgical tool 200 may be detached and removed from the disassembly fixture, if used. The surgical tool 200 may then be cleaned and tested, then delivered to a distribution center and subsequently sent to an end user (e.g., a hospital, a surgeon, an operator, etc.) for further use.

As described above with reference to FIGS. 5A and 5B, in some embodiments, the knife assembly 502 must be advanced distally B (hyper advanced) to expose the releasable connection 510 that releasably couples the distal and proximal sections 508*a,b* of the drive members 506*a,b*. It is contemplated herein, however, that the knife assembly 502 need not be advanced distally B (hyper advanced) to access and release the releasable connection. FIG. 13 is an enlarged, isometric view of a portion of the distal end of the surgical tool 200 depicting an alternative releasable connection 1302, according to one or more embodiments. More particularly, FIG. 13 depicts the interconnection between the wrist 206 and the distal end of the shaft 202 (shown in dashed lines).

As illustrated, the shaft 202 houses or otherwise includes a shaft internal structure 1304 that operatively couples the shaft 202 to the wrist 206 via a shaft adapter 1306. The releasable connection 1302 includes a crimp slot 1308 defined in the shaft internal structure 1304 and through which the pocket 706 provided in the proximal section 508*b* of each drive member 506*a,b* (only drive member 506*a* visible) may be accessed by a user (e.g., a technician). The releasable connection 1302 is exposed by advancing the shaft internal structure 1304 distally B while the shaft 202 (outer structure) remains stationary, which correspondingly advances the wrist 206 and the end effector 204 (not shown). To enable the shaft internal structure 1304 to move distally B, one or more spring pins (not shown) must first be removed from the shaft 202. Such spring pins are shown in FIG. 7A at the right side of the figure, but are omitted from FIG. 13, which depicts vacant apertures where the spring pins would otherwise be received.

As the shaft internal structure 1304 moves distally B, various drive inputs rotatably mounted to the bottom of the drive housing 208 (FIG. 2) may be rotated simultaneously. In particular, the drive inputs that are actuatable to manipulate joint cables 1310 associated with the wrist 206 may need to be rotated to allow the joint cables 1310 to dispense as the shaft internal structure 1304 moves distally B. Moreover, the drive inputs that are actuatable to manipulate the position of the knife assembly 502 (FIG. 10) may also need to be rotated to allow the knife assembly 502 to be moved distally B simultaneously with the shaft internal structure 1304.

The shaft internal structure 1304 is advanced distally B until the pocket(s) 706 are visible. Once the pocket(s) 706 are visible, the user may be able to manually access and remove the crimps 704 from the corresponding pocket 706. Removing the crimps 704 up and out of the corresponding pockets 706 effectively decouples the distal sections 508*a* of the drive members 506*a,b* from the proximal sections 508*b* enabling the knife assembly 502 to be separated from the upper and lower jaws 210, 212.

Embodiments disclosed herein include:

A. A method of replacing a consumable of a surgical tool includes securing the surgical tool, the surgical tool including a drive housing, an elongate shaft extending distally from the drive housing, an end effector arranged at a distal end of the shaft and including opposing upper and lower jaws, a wrist interposing the distal end of the shaft and the end effector, and a knife assembly including a knife arranged at the end effector and first and second drive members extending from the knife to the drive housing. The method further including uncoupling the end effector from the wrist, removing the end effector from the wrist while the wrist remains intact, removing the knife assembly from the end effector, and thereby entirely separating the end effector from proximal portions of the surgical tool, replacing the consumable of the surgical tool, reconnecting the knife assembly to the proximal portions of the surgical tool, and coupling the end effector to the wrist.

B. A surgical tool configured for a circularity processing system includes a drive housing, an elongate shaft extending distally from the drive housing, and an end effector arranged at a distal end of the shaft and including opposing upper and lower jaws pivotably attached to each other at an anvil pin, a disc receiver arranged at a proximal end of the upper and lower jaws and defining an aperture through which the anvil pin extends, and a retention pin arranged within a pin slot defined in the disc receiver and engageable with the anvil pin, wherein the retention pin is movable within the pin slot between an engaged position, where the retention pin engages the anvil pin and prevents the anvil pin from exiting the aperture, and a disengaged position, where the retention pin disengages the anvil pin and allows the anvil pin to move laterally and exit the aperture, and wherein removing the anvil pin from the aperture uncouples the upper and lower jaws.

C. A surgical tool configured for a circularity processing system includes a drive housing, an elongate shaft extending distally from the drive housing, an end effector arranged at a distal end of the shaft and including opposing upper and lower jaws pivotably attached to each other, and a concentric disc receiver arranged at a proximal end of the upper and lower jaws. The surgical tool further including a wrist interposing the distal end of the shaft and the end effector and including a disc mount provided at a distal end of the wrist, and one or more pins extending laterally through axially overlapping and concentric portions of the disc mount the concentric disc receiver to attach the end effector to the wrist, wherein removing the one or more pins allows the end effector to separate from the wrist.

D. A method of replacing a consumable of a surgical tool includes securing the surgical tool, the surgical tool including a drive housing, an elongate shaft extending distally from the drive housing and including a shaft internal structure, an end effector arranged at a distal end of the shaft and including opposing upper and lower jaws, a wrist interposing the distal end of the shaft and the end effector and operatively coupled to the shaft internal structure, and a knife assembly including a knife arranged at the end effector and first and second drive members extending from the knife to the drive housing. The method further including advancing the shaft internal structure distally relative to the shaft, and thereby advancing the wrist and the end effector, exposing first and second releasable connections provided in the shaft internal structure as the shaft internal structure moves distally, wherein each drive member includes a distal section and a proximal section releasably coupled to the distal section with the first and second releasable connections, respectively, releasing the first and second releasable connections and thereby detaching the distal sections from corresponding proximal sections of the first and second drive members, advancing the knife assembly and one or more joint cables extending through the wrist and thereby enabling removal of the knife assembly and the end effector from the wrist, removing the knife assembly from the end effector, and thereby entirely separating the end effector from proximal portions of the surgical tool, replacing the consumable of the surgical tool, reconnecting the knife assembly to the proximal portions of the surgical tool, and coupling the end effector to the wrist.

Each of embodiments A, B, C, and D may have one or more of the following additional elements in any combination: Element 1: wherein uncoupling the end effector from the wrist is preceded by removing a staple cartridge removably attached to the lower jaw. Element 2: wherein a disc mount is provided at a distal end of the wrist, and a disc receiver is provided at a proximal end of the end effector, and wherein uncoupling the end effector from the wrist comprises removing one or more pins extending laterally through axially overlapping and concentric portions of the disc mount the disc receiver. Element 3: wherein each drive member includes a distal section and a proximal section releasably coupled to the distal section with a releasable connection, and wherein removing the knife assembly from the end effector comprises moving the knife assembly distally relative to the end effector until the releasable connection becomes exposed, and releasing the releasable connection and thereby detaching the distal section from a corresponding proximal section of the first and second drive members. Element 4: wherein the releasable connection includes a knife drive spacer axially interposing and releasably coupling the distal and proximal sections, and wherein releasing the releasable connection comprises unthreading the knife drive spacer from at least one of the proximal or distal sections. Element 5: wherein the releasable connection includes a crimp fixedly attached to a cable extending within the distal section, and a pocket defined in the proximal section and sized to receive the crimp, and wherein releasing the releasable connection comprises removing the crimp from the pocket. Element 6: wherein the upper jaw is pivotably coupled to the lower jaw with an anvil pin, the method further comprising uncoupling the upper jaw from the lower jaw by removing the anvil pin. Element 7: wherein the anvil pin extends through an aperture defined in a disc receiver arranged at a proximal end of the upper and lower jaws, and a retention pin is arranged within a pin slot defined in the disc receiver and engageable with the anvil pin, and wherein removing the anvil pin comprises moving the retention pin within the pin slot from an engaged position, where the retention pin engages the anvil pin and thereby prevents the anvil pin from moving laterally, and a disengaged position, where the retention pin disengages the anvil pin and thereby allows the anvil pin to move laterally and exit the aperture. Element 8: wherein the consumable comprises one or both of the end effector and the knife assembly, and wherein replacing the consumable of the surgical tool comprises replacing one or both of the end effector and the knife assembly.

Element 9: wherein the anvil pin provides a cylindrical body having opposing first and second ends and a groove defined at or near a midpoint between the first and second ends, and wherein the retention pin is received within the groove when in the engaged position. Element 10: wherein the anvil pin further includes threading defined on the first end and threadable with a sidewall aperture defined on a first sidewall of the upper jaw, and an enlarged head provided at the second end and engageable with a second sidewall of the upper jaw when the first end is threaded to the sidewall aperture. Element 11: wherein the retention pin provides a cylindrical body having opposing first and second ends, a radial shoulder provided at the first end, and a planar surface extending from the radial shoulder to the second end, wherein the radial shoulder exhibits a diameter larger than the planar surface to help maintain the retention pin within the pin slot. Element 12: further comprising a cap plate secured to the concentric disc receiver at the pin slot and defining an aperture sized to receive a cross-sectional shape of the retention pin corresponding to the planar surface, wherein the radial shoulder prevents the retention pin from fully extending through the aperture, thus retaining the retention pin within the pin slot. Element 13: further comprising a wrist interposing the distal end of the shaft and the end effector, a disc mount provided at a distal end of the wrist, and one or more pins extending laterally through axially overlapping and concentric portions of the disc mount the concentric disc receiver to attach the end effector to the wrist. Element 14: further comprising a knife assembly including a knife arranged at the end effector, first and second drive members extending from the knife to the drive housing, wherein each drive member includes a distal section coupled to the knife and a proximal section releasably coupled to the distal section with a releasable connection. Element 15: wherein the releasable connection comprises a knife drive spacer axially interposing and releasably coupling the distal and proximal sections, wherein the knife drive spacer is threaded to at least one of the proximal or distal sections. Element 16: wherein the releasable connection comprises a crimp fixedly attached to a cable extending within the distal section, and a pocket defined in the proximal section and sized to receive the crimp, wherein the distal section is released from the proximal section by removing the crimp from the pocket.

Element 17: wherein the concentric disc receiver defines a central pocket sized and otherwise configured to receive a protrusion provided by the disc mount, and wherein co-axially aligned apertures are defined through the pocket and the protrusion to receive the one or more pins.

Element 18: wherein each releasable connection includes a crimp slot defined in the shaft internal structure and a crimp fixedly attached to a cable extending within the distal section, and a pocket defined in the proximal section and sized to receive the crimp, and wherein releasing the first and second releasable connections comprises removing the crimp from the pocket.

By way of non-limiting example, exemplary combinations applicable to A, B, C, and D include: Element 3 with Element 4; Element 3 with Element 5; Element 6 with Element 7; Element 9 with Element 10; Element 9 with Element 11; Element 11 with Element 12; Element 9 with Element 13; Element 9 with Element 14; Element 14 with Element 15; and Element 14 with Element 16.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The use of directional terms such as above, below, upper, lower, upward, downward, left, right, uphole, downhole and the like are used in relation to the illustrative embodiments as they are depicted in the figures, the upward direction being toward the top of the corresponding figure and the downward direction being toward the bottom of the corresponding figure.

What is claimed is:

1. A surgical tool, comprising:

a drive housing;

an elongate shaft extending from the drive housing;

a wrist coupled to a distal end of the elongate shaft;

an end effector coupled to a distal end of the wrist including opposing upper and lower jaws; and a knife assembly including a knife arranged at the end effector and a drive member extending from the knife to the drive housing through the wrist and the elongate shaft, the drive member including a distal section connected to a proximal section by a releasable connection, wherein the releasable connection includes a crimp fixedly attached to a cable extending through an inner channel of the distal section.

2. The surgical tool of claim 1, wherein the crimp is disposed within a pocket defined in the proximal section when the distal section is connected to the proximal section, and wherein the crimp is removable from the pocket to release the connection between the distal and proximal sections.

3. The surgical tool of claim 1, wherein the releasable connection comprises:

a knife drive spacer including an inner channel alignable with inner channels formed within the proximal and distal sections of the drive member, a first end engaged with the distal section of the drive member, and a second end having external threading engaged with internal threading of the proximal section of the drive member;

the cable extending from the knife through the aligned inner channels of the knife drive spacer and proximal and distal sections of the drive member; and wherein the crimp is engaged with the second end of the knife drive spacer and disposed within the inner channel of the proximal section.

4. A surgical tool, comprising:

a drive housing;

an elongate shaft extending from the drive housing;

a wrist coupled to a distal end of the elongate shaft;

an end effector coupled to a distal end of the wrist including opposing upper and lower jaws; and a knife assembly including a knife arranged at the end effector and a drive member extending from the knife to the drive housing through the wrist and the elongate shaft, the drive member including a distal section connected to a proximal section by a releasable connection, wherein the releasable connection comprises a knife drive spacer axially interposing and releasably coupling the distal and proximal sections, and wherein the knife drive spacer is unthreaded from either the proximal or distal section to release the connection between the distal and proximal sections.

5. The surgical tool of claim 4, the knife drive spacer further comprising external threading engageable with internal threading formed within an inner channel of either the proximal or distal sections.

6. The surgical tool of claim 5, wherein the knife drive spacer further comprises an inner channel configured to receive a cable secured to the knife drive spacer by a crimp.

7. A surgical tool, comprising:

a drive housing;

an elongate shaft extending from the drive housing;

a wrist coupled to a distal end of the elongate shaft;

an end effector coupled to a distal end of the wrist including opposing upper and lower jaws;

a knife assembly including a knife arranged at the end effector and a drive member extending from the knife to the drive housing through the wrist and the elongate shaft, the drive member including a distal section connected to a proximal section by a releasable connection;

a concentric disc receiver arranged at a proximal end of the upper and lower jaws;

a disc mount provided at a distal end of the wrist; and one or more pins extending laterally through axially overlapping and concentric sections of the disc mount and the concentric disc receiver to attach the end effector to the wrist, wherein removing the one or more pins allows the end effector to separate from the wrist.

8. The surgical tool of claim 7, wherein the concentric disc receiver defines a central pocket sized and otherwise configured to receive a protrusion provided by the disc mount, and wherein co-axially aligned apertures are defined through the pocket and the protrusion to receive the one or more pins.

9. The surgical tool of claim 1, the end effector further comprising:

an anvil pin pivotally connecting the upper and lower jaws;

a disc receiver arranged at a proximal end of the upper and lower jaws and defining an aperture through which the anvil pin extends; and a retention pin arranged within a pin slot defined in the disc receiver and engageable with the anvil pin, wherein the retention pin is movable within the pin slot between an engaged position, where the retention pin engages the anvil pin and prevents the anvil pin from exiting the aperture, and a disengaged position, where the retention pin disengages the anvil pin and allows the anvil pin to move laterally and exit the aperture, and wherein removing the anvil pin from the aperture uncouples the upper and lower jaws.

10. A surgical tool, comprising:

a drive housing;

an elongate shaft extending from the drive housing;

a shaft internal structure disposed in the elongate shaft and moveable relative to the elongate shaft between a first and a second position, the shaft internal structure including a slot occluded by the elongate shaft in the first position and exposed in the second position;

a wrist coupled to a distal end of the shaft internal structure;

an end effector coupled to a distal end of the wrist including opposing upper and lower jaws;

a knife assembly including a knife arranged at the end effector and a drive member extending from the knife to the drive housing through the wrist and shaft internal structure, the drive member including a distal section connected to a proximal section by a releasable connection, wherein the releasable connection is accessible through the exposed slot when the shaft internal structure is in the second position to release the connection between the proximal and distal sections.

11. The surgical tool of claim 10, further comprising:

an adapter interposing the wrist and the shaft internal structure, wherein the wrist is coupled to the distal end of the shaft internal structure by the adapter.

12. The surgical tool of claim 10, wherein the releasable connection comprises a crimp fixedly attached to a cable extending through an inner channel of the distal section that is disposable within a pocket defined in the proximal section, wherein the slot and pocket are aligned to provide access to the crimp when the shaft internal structure is in the second position.

13. The surgical tool of claim 10, further comprising:

a plurality of joint cables extending through the wrist and shaft internal structure to a corresponding drive input of the drive housing, wherein the drive inputs are rotatable to dispense the plurality of joint cables as the shaft internal structure moves from the first position to the second position.

14. The surgical tool of claim 10, further comprising:

a spring pin extending through the shaft and internal shaft structure, wherein the spring pin is removed from the shaft and shaft internal structure to allow movement of the shaft internal structure from the first position to the second position.

15. A method of replacing a consumable of a surgical tool, comprising:

securing the surgical tool, the surgical tool including:

a drive housing;

an elongate shaft extending distally from the drive housing;

a shaft internal structure disposed within the elongated shaft;

an end effector arranged at a distal end of the shaft and including opposing upper and lower jaws;

a wrist interposing the distal end of the shaft and the end effector and operatively coupled to the shaft internal structure; and a knife assembly including a knife arranged at the end effector and first and second drive members extending from the knife to the drive housing;

advancing the shaft internal structure distally relative to the elongated shaft, and thereby advancing the wrist and the end effector;

exposing first and second releasable connections provided in the shaft internal structure as the shaft internal structure moves distally, wherein each drive member includes a distal section releasably coupled to a proximal section by the first and second releasable connections, respectively; and releasing the first and second releasable connections and thereby detaching the distal sections from corresponding proximal sections of the first and second drive members.

16. The method of claim 15, further comprising:

advancing the knife assembly and one or more joint cables extending through the wrist and thereby enabling removal of the knife assembly and the end effector from the wrist; and removing the knife assembly from the end effector, and thereby entirely separating the end effector from proximal sections of the surgical tool.

17. The method of claim 16, further comprising:

replacing the knife assembly of the surgical tool; and reconnecting the knife assembly to the proximal sections of the surgical tool by reconnecting the first and second releasable connections.

18. The method of claim 17, further comprising coupling the end effector to the wrist.

19. The method of claim 15, wherein each releasable connection includes a crimp slot defined in the shaft internal structure, a crimp fixedly attached to a cable extending within a corresponding distal section, and a pocket sized to receive the crimp defined in the corresponding proximal section, wherein releasing the first and second releasable connections comprises removing the crimp from the corresponding pocket.

20. The method of claim 15, wherein the surgical tool comprises an adapter interposing the wrist and shaft internal structure.

21. A surgical tool, comprising:

a drive housing;

an elongate shaft extending from the drive housing;

a wrist coupled to a distal end of the elongate shaft;

an end effector coupled to a distal end of the wrist including opposing upper and lower jaws, the end effector including:

an anvil pin pivotally connecting the upper and lower jaws;

a disc receiver arranged at a proximal end of the upper and lower jaws and defining an aperture through which the anvil pin extends; and a retention pin arranged within a pin slot defined in the disc receiver and engageable with the anvil pin, wherein the retention pin is movable within the pin slot between an engaged position, where the retention pin engages the anvil pin and prevents the anvil pin from exiting the aperture, and a disengaged position, where the retention pin disengages the anvil pin and allows the anvil pin to move laterally and exit the aperture, and wherein removing the anvil pin from the aperture uncouples the upper and lower jaws; and a knife assembly including a knife arranged at the end effector and a drive member extending from the knife to the drive housing through the wrist and the elongate shaft, the drive member including a distal section connected to a proximal section by a releasable connection.

* * * * *